United States Patent
Dakka et al.

(10) Patent No.: US 9,556,103 B2
(45) Date of Patent: Jan. 31, 2017

(54) BIPHENYL ESTERS, THEIR PRODUCTION AND THEIR USE IN THE MANUFACTURE OF PLASTICIZERS

(71) Applicant: ExxonMobil Chemical Patents Inc., Baytown, TX (US)

(72) Inventors: Jihad M. Dakka, Whitehouse Station, NJ (US); Wei Tang, New York, NY (US); Stephen Zushma, Clinton, NJ (US); Christine A. Costello, Easton, PA (US); Diana Smirnova, Spring, TX (US); Madhavi Vadlamudi, Clinton, NJ (US); Victor DeFlorio, Cranford, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/722,638

(22) Filed: May 27, 2015

(65) Prior Publication Data

US 2015/0361027 A1 Dec. 17, 2015

Related U.S. Application Data

(60) Provisional application No. 62/012,037, filed on Jun. 13, 2014.

(51) Int. Cl.
| | |
|---|---|
| *C07C 67/00* | (2006.01) |
| *C07C 67/035* | (2006.01) |
| *C07C 67/08* | (2006.01) |
| *C07C 69/76* | (2006.01) |
| *C08K 5/00* | (2006.01) |

(52) U.S. Cl.
CPC ............. *C07C 67/035* (2013.01); *C07C 67/08* (2013.01); *C07C 69/76* (2013.01); *C08K 5/00* (2013.01)

(58) Field of Classification Search
CPC ........ C07C 67/035; C07C 67/08; C07C 69/76; C07C 69/78; C07C 69/157; C07C 2101/16; C07C 67/39; C08K 5/00
See application file for complete search history.

(56) References Cited

U.S. PATENT DOCUMENTS

| | | | |
|---|---|---|---|
| 2,520,084 A | 8/1950 | Dazzi | |
| 2,634,248 A | 4/1953 | Dazzi | |
| 3,928,481 A | 12/1975 | Suggitt | |
| 3,928,484 A | 12/1975 | Suggitt | |
| 3,962,362 A | 6/1976 | Suggitt | |
| 4,695,651 A | 9/1987 | Higuchi et al. | |
| 5,380,460 A | 1/1995 | Wand et al. | |
| 5,523,473 A | 6/1996 | Saitou et al. | |
| 6,175,038 B1 | 1/2001 | Jhung et al. | |
| 6,740,254 B2 | 5/2004 | Zhou et al. | |
| 6,777,514 B2 | 8/2004 | Patil et al. | |
| 7,297,738 B2 | 11/2007 | Gosse et al. | |
| 7,579,511 B1 | 8/2009 | Dakka et al. | |
| 8,829,093 B2 | 9/2014 | Dakka et al. | |
| 2002/0193631 A1 | 12/2002 | Park et al. | |
| 2006/0247461 A1 | 11/2006 | Schlosberg et al. | |
| 2008/0242895 A1 | 10/2008 | Godwin et al. | |
| 2010/0159177 A1 | 6/2010 | Dakka et al. | |
| 2014/0212666 A1 | 7/2014 | Dakka et al. | |
| 2014/0272626 A1 | 9/2014 | Berlowitz et al. | |
| 2014/0275605 A1 | 9/2014 | Dakka et al. | |
| 2014/0275606 A1 | 9/2014 | Bai et al. | |
| 2014/0275607 A1 | 9/2014 | Dakka et al. | |
| 2014/0275609 A1 | 9/2014 | Dakka et al. | |
| 2014/0315021 A1 | 10/2014 | Naert et al. | |
| 2014/0316155 A1 | 10/2014 | Dakka et al. | |
| 2014/0378697 A1 | 12/2014 | de Smit et al. | |
| 2015/0080545 A1 | 3/2015 | Dakka et al. | |
| 2015/0080546 A1 | 3/2015 | Dakka et al. | |

FOREIGN PATENT DOCUMENTS

| | | | |
|---|---|---|---|
| JP | 01313455 | * | 12/1989 |
| JP | 2003-246767 | | 9/2003 |
| JP | 2004-051528 | | 2/2004 |
| WO | WO 99/32427 | | 7/1999 |
| WO | WO 03/029339 | | 4/2003 |
| WO | WO 2004/046078 | | 6/2004 |

OTHER PUBLICATIONS translated 455, 1989.*
Godwin, A.D. et al., "*Plasticizers*," Applied Polymer Science: 21$^{st}$ Century, Elsevier 2000, pp. 157-175.
Kulev et al., "*Esters of diphenic acid and their plasticizing properties*," Izvestiya Tomskogo Politekhnicheskogo Instituta (1961), 111.
Shioda et al., "*Synthesis of dialkyl diphenates and their properties*," Yuki Gosei Kagaku Kyokaishi (1959), 17.
U.S. Appl. No. 62/012,024, filed Jun. 13, 2014, Salciccioli et al.
U.S. Appl. No. 62/012,037, filed Jun. 13, 2014, Dakka et al.
U.S. Appl. No. 62/026,889, filed Jan. 27, 2015, Dakka et al.
U.S. Appl. No. 62/068,144, filed Oct. 24, 2014, Dakka et al.
U.S. Appl. No. 62/094,218, filed Dec. 19, 2014, Salciccioli et al.

(Continued)

*Primary Examiner* — Yevegeny Valenrod
*Assistant Examiner* — Blaine G Doletski

(57) ABSTRACT

A biphenyl diester useful as a plasticizer having the formula (I):

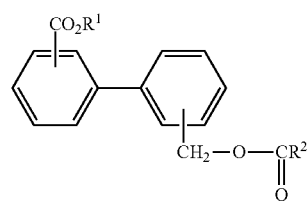

wherein $R^1$ is an alkyl group having 5 to 15 carbon atoms and $R^2$ is a methyl group or a phenyl group.

22 Claims, 5 Drawing Sheets

(56) References Cited

OTHER PUBLICATIONS

U.S. Appl. No. 62/137,996, filed Mar. 25, 2015, Salciccioli et al.
U.S. Appl. No. 62/138,179, filed Mar. 25, 2015, Evans et al.
U.S. Appl. No. 62/140,723, filed Mar. 31, 2015, Salciccioli et al.
U.S. Appl. No. 62/320,014, filed Apr. 8, 2016, Dakka et al.
U.S. Appl. No. 14/516,239, filed Oct. 16, 2014, Dakka et al.
Hoefnagel et al., "Selective alkylation of methylbenzenes with cyclohexene catalyzed by solid acids," Catalysis Letters, vol. 85, No. 1-2, 2003, pp. 7-11.
Kamiyama, T. et al., "Catalysts for the Hydroalkylation of Benzene, Toluene and Xylenes," Chem. Pharm. Bull., 1981, vol. 29(1), pp. 15-24.
Koshel, G.N. et al., "Liquid-Phase Catalytic Oxidation of Methyl Derivatives of Biphenyl," Kinetics and Catalysis, 2004, vol. 45, No. 6, pp. 821-825.
Lu et al., "Selective Hydrogenation of Single Benzene Ring in Biphenyl Catalyzed by Skeletal Ni," ChemCatChem., 2009, vol. 1(3), pp. 369-371.
Suga, K. et al., Selective Oxygenation of 4,4'-Dimethylbiphenyl with Molecular Oxygen, Catalyzed by 9-Phenyl-10-methylacridinium Ion via Photoinduced Electron Transfer, J. Phys. Chem. A, 2005, vol. 109, pp. 10168-10175.
Sherman et al., "Dimethylbiphenyls from toluene," American Chemical Society, Chemical Innovation, 2000, pp. 25-30.
Kondratov,V.K. et al., "Preparation of 4,4'-diphenyldicarboxylic acid," Khimicheskaya Promyshlennost, Moscow, Russian Federation, 1974, vol. 8, pp. 585-586 (Abstract).

* cited by examiner

BIPHENYL ESTERS, THEIR PRODUCTION AND THEIR USE IN THE MANUFACTURE OF PLASTICIZERS

PRIORITY

This invention claims priority to and the benefit of U.S. Ser. No. 62/012,037, filed Jun. 13, 2014.

FIELD OF INVENTION

The disclosure relates to biphenyl esters, their production and their use in the manufacture of plasticizers.

BACKGROUND OF INVENTION

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Esters based on cyclohexanoic acid have also been proposed for use as plasticizers for PVC. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427; WO 2004/046078; WO 2003/029339; US 2006-0247461; and U.S. Pat. No. 7,297,738.

Other suggested plasticizers include esters based on benzoic acid (see, for instance, U.S. Pat. No. 6,740,254) and polyketones, such as described in U.S. Pat. No. 6,777,514; and US 2008-0242895. Epoxidized soybean oil, which has much longer alkyl groups ($C_{16}$ to $C_{18}$), has been tried as a plasticizer, but is generally used as a PVC stabilizer. Stabilizers are used in much lower concentrations than plasticizers. US 2010-0159177 discloses triglycerides with a total carbon number of the triester groups between 20 and 25, produced by esterification of glycerol with a combination of acids derived from the hydroformylation and subsequent oxidation of $C_3$ to $C_9$ olefins. These are said to have excellent compatibility with a wide variety of resins.

However, despite these advances, typically the best that has been achieved is a flexible PVC article having either reduced performance or poorer processability. Thus, existing efforts to make new plasticizer systems for PVC have not proven to be entirely satisfactory, and so this is still an area of intense research.

One other potential route to PVC plasticizers is the production of biphenyl esters. For example, in an article entitled "Esters of diphenic acid and their plasticizing properties", Kulev et al., *Izvestiya Tomskogo Politekhnicheskogo Instituta* (1961), 111, disclose that diisoamyl diphenate, bis(2-ethylhexyl) diphenate and mixed heptyl, octyl and nonyl diphenates can be prepared by esterification of diphenic acid, and allege that the resultant esters are useful as plasticizers for vinyl chloride. Similarly, in an article entitled "Synthesis of dialkyl diphenates and their properties", Shioda et al., *Yuki Gosei Kagaku Kyokaishi* (1959), 17, disclose that dialkyl diphenates of $C_1$ to $C_8$ alcohols, said to be useful as plasticizers for poly(vinyl chloride), can be formed by converting diphenic acid to diphenic anhydride and esterifying the diphenic anhydride. However, since these processes involve esterification of diphenic acid or anhydride, they necessarily result in 2,2'-substituted diesters of diphenic acid. Generally, such diesters having substitution on the 2-carbons have proven to be too volatile for use as plasticizers.

SUMMARY OF THE INVENTION

In accordance with the present invention, it has now been found that novel biphenyl diesters having different ester groups on the phenyl rings can be produced by a process including the controlled oxidation of dimethylbiphenyl in the presence of acetic acid or benzoic acid as a solvent. In the case of an acetic acid solvent, the oxidation not only produces diphenic acid but also produces significant quantities of a biphenyl compound having an acetate group on one phenyl ring and a carboxylic acid on the other phenyl ring. Esterification of the carboxylic acid group with a long chain alcohol produces a biphenyl diester with an acetate group on one phenyl ring and a long chain ester on the other phenyl ring. The resulting diester is found to exhibit an attractive combination of low volatility and good processability, low temperature performance and PVC compatibility.

Thus, in one aspect, the invention resides in a biphenyl diester having the formula (I):

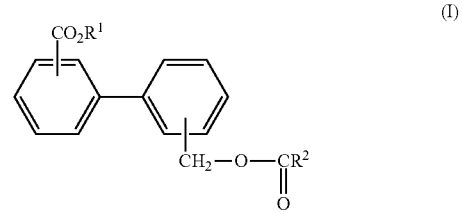

wherein $R^1$ is an alkyl group having 5 to 15 carbon atoms and $R^2$ is a methyl group or a phenyl group.

In a further aspect, the invention resides in a process for producing a biphenyl diester of formula (I), the process comprising:
(a) contacting a dimethyl biphenyl compound having the formula (II):

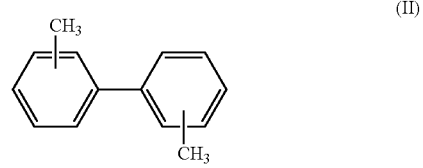

with an oxidizing agent in the presence of a solvent comprising acetic acid and/or benzoic acid under conditions effective to oxidize at least part of the dimethyl biphenyl compound to produce an oxidation product comprising a biphenyl monoester having the formula (III):

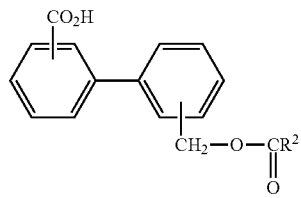

(III)

wherein $R^2$ is a methyl group or a phenyl group; and (b) reacting at least part of the biphenyl monoester having the formula (III) with an alcohol having 5 to 15 carbon atoms under conditions effective to produce said biphenyl diester.

DETAILED DESCRIPTION OF THE EMBODIMENTS

Figure 1:
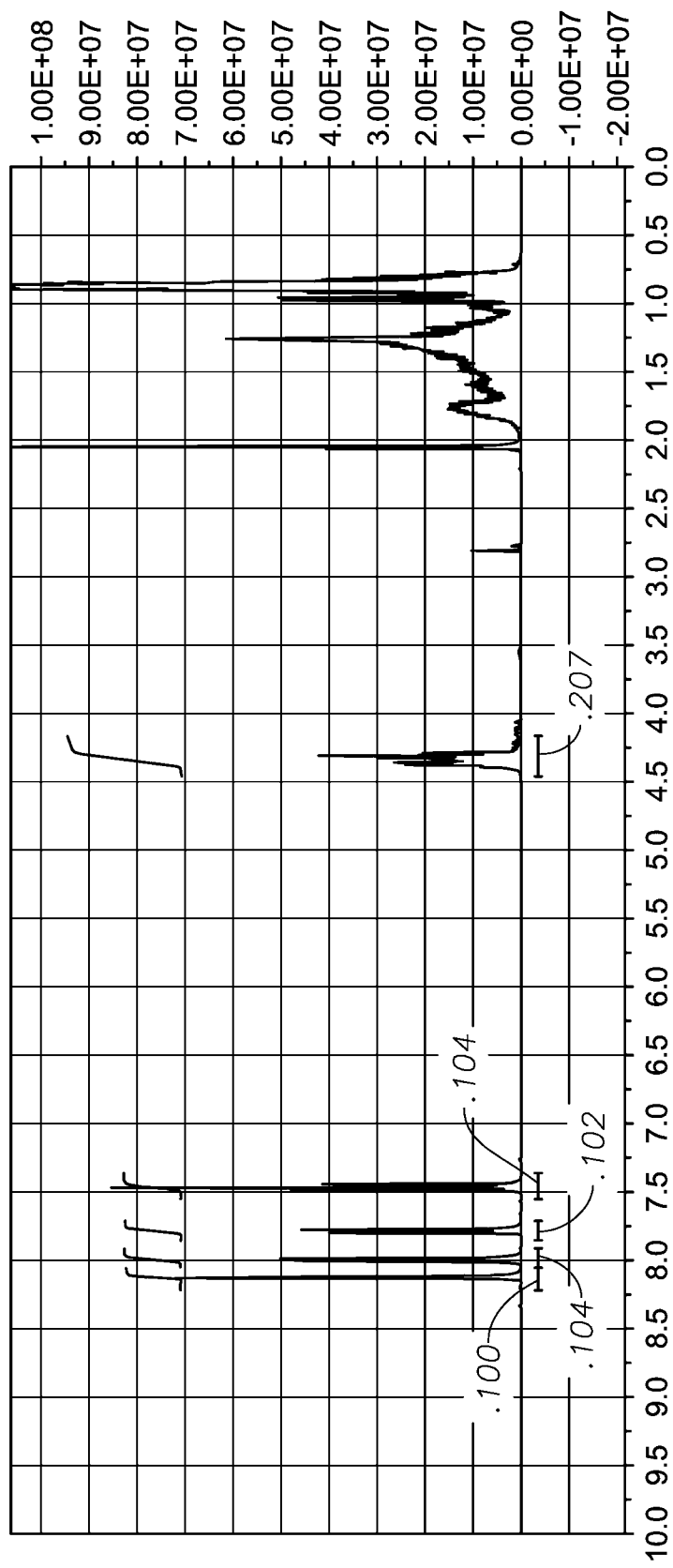
FIG. 1 is the $^1$H NMR spectrum of 3-bromo-benzoic acid, isononyl ester as produced in step (a) of the method of Example 1.

A novel biphenyl ester useful as a plasticizer for PVC and other polymer resins is disclosed herein together with a method of producing the same. In particular, the present biphenyl ester has the formula (I):

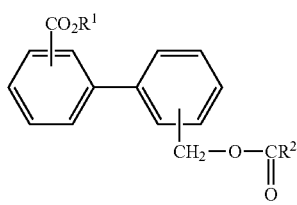

(I)

wherein $R^1$ is an alkyl group having from 5 to 15 carbon atoms, such as from 7 to 14 carbon atoms, for example from 9 to 13 carbon atoms and $R^2$ is a methyl group or a phenyl group. In one preferred embodiment, $R^2$ is a methyl group. In an embodiment, $R^1$ has 5, 6, 7, 8, 9, 10, 11, 12, 13, 14, and/or 15 carbon atoms.

In an embodiment described herein, $R^1$ may be one or more of pentyl, hexyl, heptyl, octyl, nonyl, decyl, undecyl, or dodecyl.

It will be appreciated that the biphenyl ester of formula (I) can exist as a number of isomeric forms depending on the locations of the ester groups on their respective phenyl rings. In some embodiments, where the biphenyl ester is prepared by a process that yields an isomeric mixture, it may be preferred that the mixture comprises less than 10 wt % of the 2,X' isomers, where X' is 2', 3' or 4'. For example, it may be preferred that the mixture comprises at least 50 wt % of the 3,3', 3,4', and 4,4' isomers.

One suitable process for producing the biphenyl diester of formula (I) comprises reacting a dimethyl biphenyl compound having the formula (II):

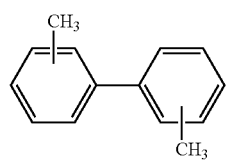

(II)

with oxygen in the presence of a solvent comprising acetic acid and/or benzoic acid, preferably acetic acid, under conditions effective to oxidize at least part of the dimethyl biphenyl compound to produce an oxidation product comprising a biphenyl monoester having the formula (III):

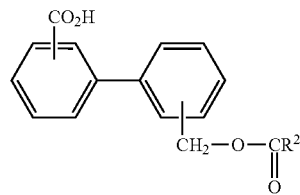

(III)

wherein $R^2$ is a methyl group or a phenyl group. The oxidation reaction may be conducted at a temperature from 50 to 200° C., such as from 90 to 170° C., in the presence of a catalyst comprising cobalt and/or manganese and/or one or more compounds thereof. Relatively high concentration of high catalyst oxidation state e.g., Co (III) and low oxygen pressure favor the formation of the monoester of formula (III). Thus it may be desirable to conduct the oxidation reaction at a molar ratio of dimethyl biphenyl compound to cobalt and/or manganese catalyst from 1:0.1 to 1:1 and/or an oxygen concentration in the gas phase of less than 5% by volume.

The resultant biphenyl monoester can then be esterified with an alcohol having 5 to 15 carbon atoms (such as 5, 6, 7, 8, 9, 10, 11, 12, 13, 14, and/or 15 carbon atoms) to produce the desired biphenyl diester, with or without separating the monoester from the acid medium used for the oxidation process. Suitable conditions for the esterification reaction include a temperature from 20 to 300° C., such as from 150 to 250° C., optionally in the presence of a presence of a catalyst, such as a Lewis acid catalyst, e.g., a titanium alkoxide.

Any known method can be used to produce the dimethyl biphenyl compound having the formula (II) used as a precursor in the above process, but in one preferred embodiment the dimethyl biphenyl precursor is produced by hydroalkylation of toluene to produce (methylcyclohexyl) toluene (MCHT) followed by dehydrogenation of the MCHT.

Hydroalkylation of toluene to MCHT involves reacting toluene with hydrogen in the presence of the catalyst in accordance with the following equation:

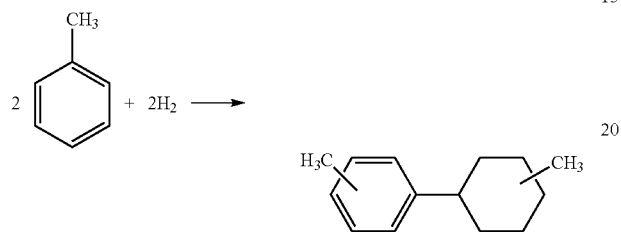

The catalyst employed in the hydroalkylation reaction is a bifunctional catalyst comprising a hydrogenation component and a solid acid alkylation component, typically a molecular sieve. The catalyst may also include a binder such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Any known hydrogenation metal or compound thereof can be employed as the hydrogenation component of the catalyst, although suitable metals include palladium, ruthenium, nickel, zinc, tin, and cobalt, with palladium being particularly advantageous. In certain embodiments, the amount of hydrogenation metal present in the catalyst is between about 0.05 and about 10 wt %, such as between about 0.1 and about 5 wt %, of the catalyst.

In one embodiment, the solid acid alkylation component comprises a large pore molecular sieve having a Constraint Index (as defined in U.S. Pat. No. 4,016,218) less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-4 is described in U.S. Pat. No. 4,021,447. Zeolite ZSM-20 is described in U.S. Pat. No. 3,972,983. Zeolite Beta is described in U.S. Pat. No. 3,308,069, and Re. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

In another, more preferred embodiment, the solid acid alkylation component comprises a molecular sieve of the MCM-22 family. The term "MCM-22 family material" (or "material of the MCM-22 family" or "molecular sieve of the MCM-22 family"), as used herein, includes one or more of:
molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);
molecular sieves made from a common second degree building block, being a 2-dimensional tiling of such MWW framework topology unit cells, forming a monolayer of one unit cell thickness, preferably one c-unit cell thickness;
molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and
molecular sieves made by any regular or random 2-dimensional or 3-dimensional combination of unit cells having the MWW framework topology.

Molecular sieves of the MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0293032), ITQ-1 (described in U.S. Pat. No. 6,077,498), ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof.

In addition to the toluene and/or xylene and hydrogen, a diluent, which is substantially inert under hydroalkylation conditions, may be included in the feed to the hydroalkylation reaction. In certain embodiments, the diluent is a hydrocarbon, in which the desired cycloalkylaromatic product is soluble, such as a straight chain paraffinic hydrocarbon, a branched chain paraffinic hydrocarbon, and/or a cyclic paraffinic hydrocarbon. Examples of suitable diluents are decane and cyclohexane. Although the amount of diluent is not narrowly defined, desirably the diluent is added in an amount such that the weight ratio of the diluent to the aromatic compound is at least 1:100; for example at least 1:10, but typically no more than 10:1, desirably no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. The molar ratio of hydrogen to aromatic feed is typically from about 0.15:1 to about 15:1.

In the present process, it is found that MCM-22 family molecular sieves are particularly active and stable catalysts for the hydroalkylation of toluene or xylene. In addition, catalysts containing MCM-22 family molecular sieves exhibit improved selectivity to the 3,3'-dimethyl, the 3,4'-dimethyl, the 4,3'-dimethyl and the 4,4'-dimethyl isomers in the hydroalkylation product, while at the same time reducing the formation of fully saturated and heavy by-products. For example, using an MCM-22 family molecular sieve with a toluene feed, it is found that the hydroalkylation reaction product may comprise:

at least 60 wt %, such as at least 70 wt %, for example at least 80 wt % of the 3,3', 3,4', 4,3' and 4,4'-isomers of (methylcyclohexyl)toluene based on the total weight of all the (methylcyclohexyl)toluene isomers;

less than 40 wt %, such as less than 30 wt %, for example from 0 to 20 wt % of the 2,2', 2,3', and 2,4'-isomers of (methylcyclohexyl)toluene based on the total weight of all the (methylcyclohexyl)toluene isomers;

less than 30 wt % of methylcyclohexane and less than 2% of dimethylbicyclohexane compounds;

and less than 1 wt % of compounds containing in excess of 14 carbon atoms.

The hydroalkylation reaction product may also contain significant amounts of residual toluene, for example up to 90 wt %, such as up to 80 wt %, typically from 60 to 80 wt % of residual toluene based on the total weight of the hydroalkylation reaction product. Thus, the major components of the hydroalkylation reaction effluent are (methylcyclohexyl)toluenes, residual toluene and fully saturated single ring by-product (methylcyclohexane). The residual toluene and light by-products can readily be removed from the reaction effluent by, for example, distillation. The residual toluene can then be recycled to the hydroalkylation reactor, while the saturated by-products can be dehydrogenated to produce additional recyclable feed.

The remainder of the hydroalkylation reaction effluent, composed mainly of (methylcyclohexyl)toluenes, is then dehydrogenated to convert the (methylcyclohexyl)toluenes to the corresponding methyl-substituted biphenyl compounds. The dehydrogenation is conveniently conducted at a temperature from about 200° C. to about 600° C. and a pressure from about 100 kPa to about 3550 kPa (atmospheric to about 500 psig) in the presence of dehydrogenation catalyst. A suitable dehydrogenation catalyst comprises one or more elements or compounds thereof selected from Group 10 of the Periodic Table of Elements, for example platinum, on a support, such as silica, alumina or carbon nanotubes. In one embodiment, the Group 10 element is present in an amount of from 0.1 to 5 wt % of the catalyst. In some cases, the dehydrogenation catalyst may also include tin or a tin compound to improve the selectivity to the desired methyl-substituted biphenyl product. In one embodiment, the tin is present in an amount of from 0.05 to 2.5 wt % of the catalyst.

Particularly using an MCM-22 family-based catalyst for the upstream hydroalkylation reaction, the product of the dehydrogenation step comprises dimethylbiphenyl compounds in which the concentration of the 3,3'-, 3,4'-, and 4,4' isomers is at least 50 wt %, such as at least 60 wt %, for example at least 70 wt % based on the total weight of dimethylbiphenyl compounds. Typically, the concentration of the 2,X'-dimethylbiphenyl isomers in the dehydrogenation product is less than 40 wt %, such as less than 30 wt %, for example from 0 to 20 wt % based on the total weight of dimethylbiphenyl compounds.

This invention further relates to:

1. A biphenyl diester having the formula (I):

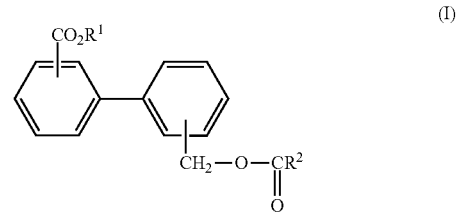

wherein $R^1$ is an alkyl group having 5 to 15 carbon atoms and $R^2$ is a methyl group or a phenyl group.

2. The biphenyl diester of paragraph 1, wherein $R^1$ is an alkyl group having 7 to 14 carbon atoms.

3. The biphenyl diester of paragraph 1 or paragraph 2, wherein $R^1$ is an alkyl group having 9 to 13 carbon atoms.

4. The biphenyl diester of any preceding paragraph, wherein $R^2$ is a methyl group.

5. An isomeric mixture of biphenyl diesters of any preceding paragraph and comprising less than 10 wt % of the 2,X' isomers, where X' is 2', 3' or 4'.

6. A process for producing the biphenyl diester of paragraph 1, the process comprising:

contacting a dimethyl biphenyl compound having the formula (II):

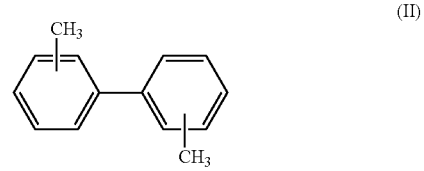

with oxygen in the presence of a solvent comprising acetic acid and/or benzoic acid under conditions effective to oxidize at least part of the dimethyl biphenyl compound to produce an oxidation product comprising a biphenyl monoester having the formula (III):

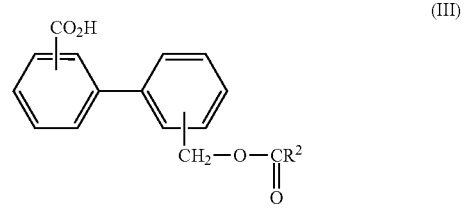

wherein $R^2$ is a methyl group or a phenyl group; and (b) reacting at least part of the biphenyl monoester having the formula (III) with an alcohol having 5 to 15 carbon atoms under conditions effective to produce said biphenyl diester.

7. The process of paragraph 6, wherein the carboxylic acid solvent comprises acetic acid.

8. The process of paragraph 6 or paragraph 7, wherein the conditions in the contacting (a) include a temperature from 50 to 200° C.

9. The process of any one of paragraphs 6 to 8, wherein the contacting (a) is conducted in the presence of a catalyst comprising cobalt and/or manganese.

10. The process of paragraph 9, wherein the contacting (a) is conducted at a molar ratio of dimethyl biphenyl compound to catalyst from 1:0.1 to 1:1.

11. The process of any one of paragraphs 6 to 10, wherein the oxygen concentration in the gas phase during the contacting (a) is less than 5% by volume.

12. The process of any one of paragraphs 6 to 11 and further comprising:
(c) separating at least part of the biphenyl monoester having the formula (III) from the oxidation product prior to (b).

13. The process of any one of paragraphs 6 to 12 and further comprising:
(d) contacting a feed comprising toluene and hydrogen with a hydroalkylation catalyst under conditions effective to produce a hydroalkylation product comprising (methylcyclohexyl)toluene; and
(e) dehydrogenating at least part of the hydroalkylation product in the presence of a dehydrogenation catalyst under conditions effective to produce a dehydrogenation product comprising a dimethyl biphenyl compound having the formula (II).

14. The process of paragraph 13, wherein the hydroalkylation catalyst comprises an acidic component and a hydrogenation component.

15. The process of paragraph 14, wherein the acidic component of the hydroalkylation catalyst comprises a molecular sieve.

16. The process of paragraph 15, wherein the molecular sieve is selected from the group consisting of BEA, FAU and MTW structure type molecular sieves, molecular sieves of the MCM-22 family and mixtures thereof.

17. The process of paragraph 15, wherein the molecular sieve comprises a molecular sieve of the MCM-22 family.

18. The process of any one of paragraphs 14 to 17, wherein the hydrogenation component of the hydroalkylation catalyst selected from the group consisting of palladium, ruthenium, nickel, zinc, tin, cobalt and compounds and mixtures thereof.

19. The process of any one of paragraphs 13 to 18, wherein the conditions in (d) include a temperature from about 100° C. to about 400° C. and a pressure from about 100 to about 7,000 kPa.

The invention will now be more particularly described with reference to the following non-limiting Examples and the accompanying drawings.

Example 1

Synthesis of 4'-acetoxymethylbiphenyl-3-carboxylic acid, isononyl ester

In order to test its properties as a plasticizer, a sample of 4'-acetoxymethylbiphenyl-3-carboxylic acid, isononyl ester was produced from 3-bromobenzoic acid by the following laboratory synthesis method.

(a) 3-Bromobenzoic acid (25 g, 0.124 mmol) and Exxal 9 isononyl alcohol (53.8 g, 0.372 mmol) were charged to a 250 ml round bottom flask and purged with $N_2$ for 20 minutes. The mixture was heated to 185° C. and a tin(II) 2-ethylhexanoate (66.4 mg) catalyst was added to the mixture. Heating was continued until the reaction mixture reached 220° C. The mixture was maintained 220° C. for 2 hrs for the reaction to proceed. The reaction was then cooled and excess Exxal 9 alcohol was removed by vacuum distillation. $^1$H NMR of the product, 3-bromo-benzoic acid, isononyl ester (formula IV)

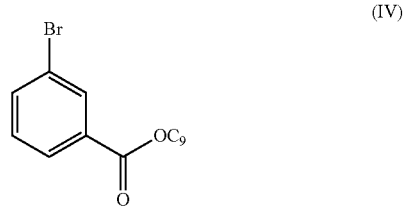

is shown in FIG. 1.

(b) 3-Bromo-benzoic acid, isononyl ester (23 g, 70 mmol) from (a), 4-hydroxymethylphenylboronic acid (12.8 g, 84 mmol), potassium carbonate aqueous solution (19.3 g in 100 ml DI water), isopropanol (150 ml) and tetrakis(triphenylphosphine)palladium(0) (0.81 g) were charged to a 250 ml round bottom flask. The mixture was purged with $N_2$ for 30 min and then heated under reflux for 2 days. The reaction was then stopped and the contents of the flask were washed with water and then dried over magnesium sulfate. Product was collected by rotavaping the solvent and drying in a vacuum oven. $^1$H NMR of the product, 4'-hydroxymethyl-biphenyl-3-carboxylic acid, isononyl ester (formula V)

Figure 2:
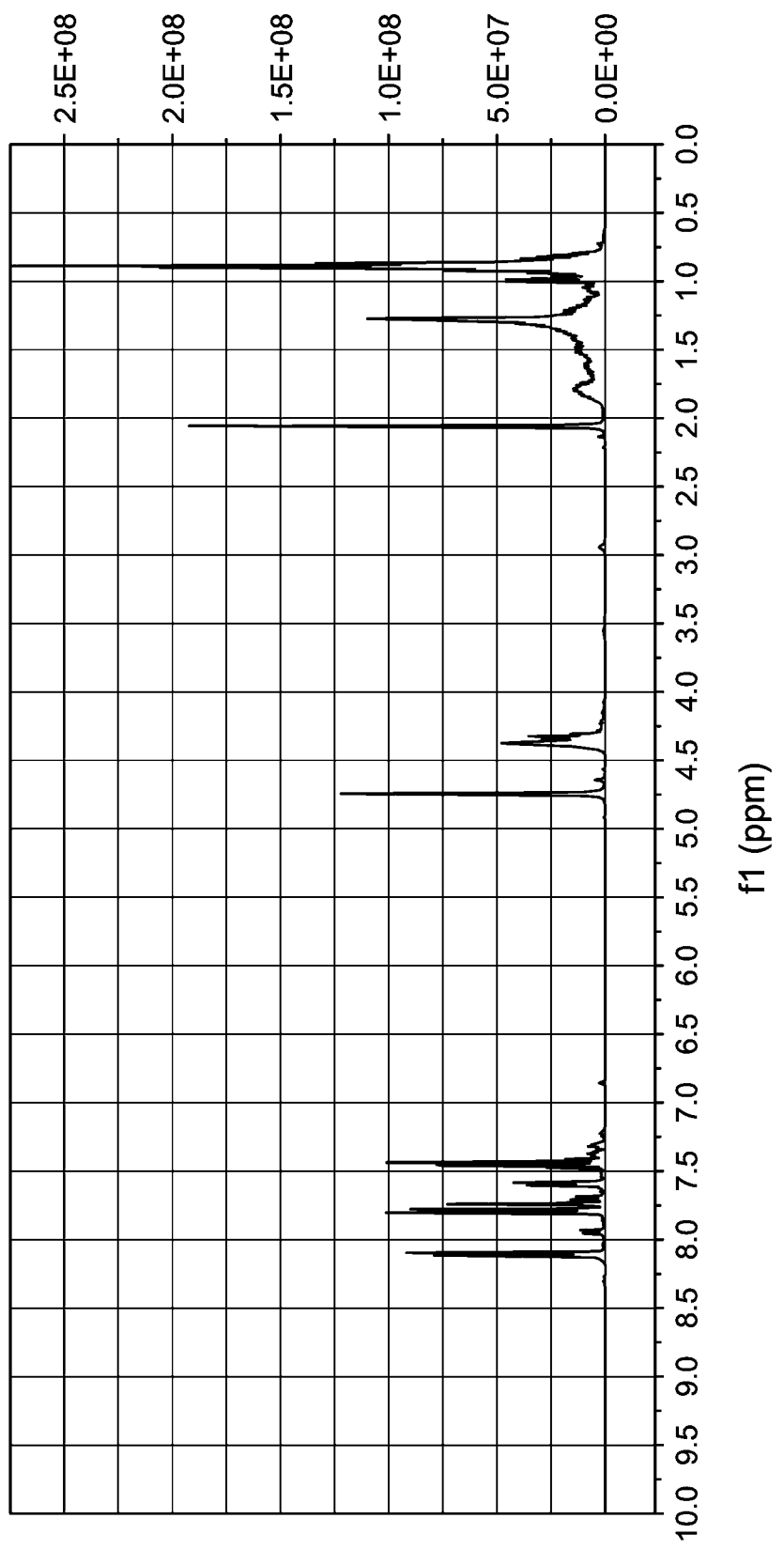
FIG. 2 is the $^1$H NMR spectrum of 4'-hydroxymethylbiphenyl-3-carboxylic acid, isononyl ester as produced in step (b) of the method of Example 1.

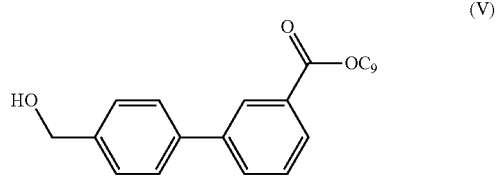

is shown in FIG. 2.

(c) 4'-hydroxymethylbiphenyl-3-carboxylic acid, isononyl ester (30 g, 89.5 mol) from (b) and triethylamine (18.7 ml) were dissolved in 180 ml acetone in a 500 ml round bottom flask. The solution was cooled down with an ice bath. Acetyl chloride (9.6 ml, 134 mmol) was added to the solution dropwise. The solution was then heated to 60° C. for 4 hr. The reaction was then stopped, and the mixture diluted with water and cooled down. The salts were filtered out. The solution was washed with water three times, dried over magnesium sulfate, and the solvent removed by a rotary evaporator. The final product was further dried in vacuum oven. $^1$H NMR of the product, 4'-acetoxymethylbiphenyl-3-carboxylic acid, isononyl ester (formula VI)

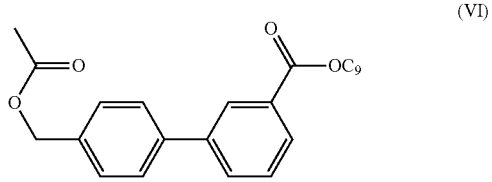

Figure 3:
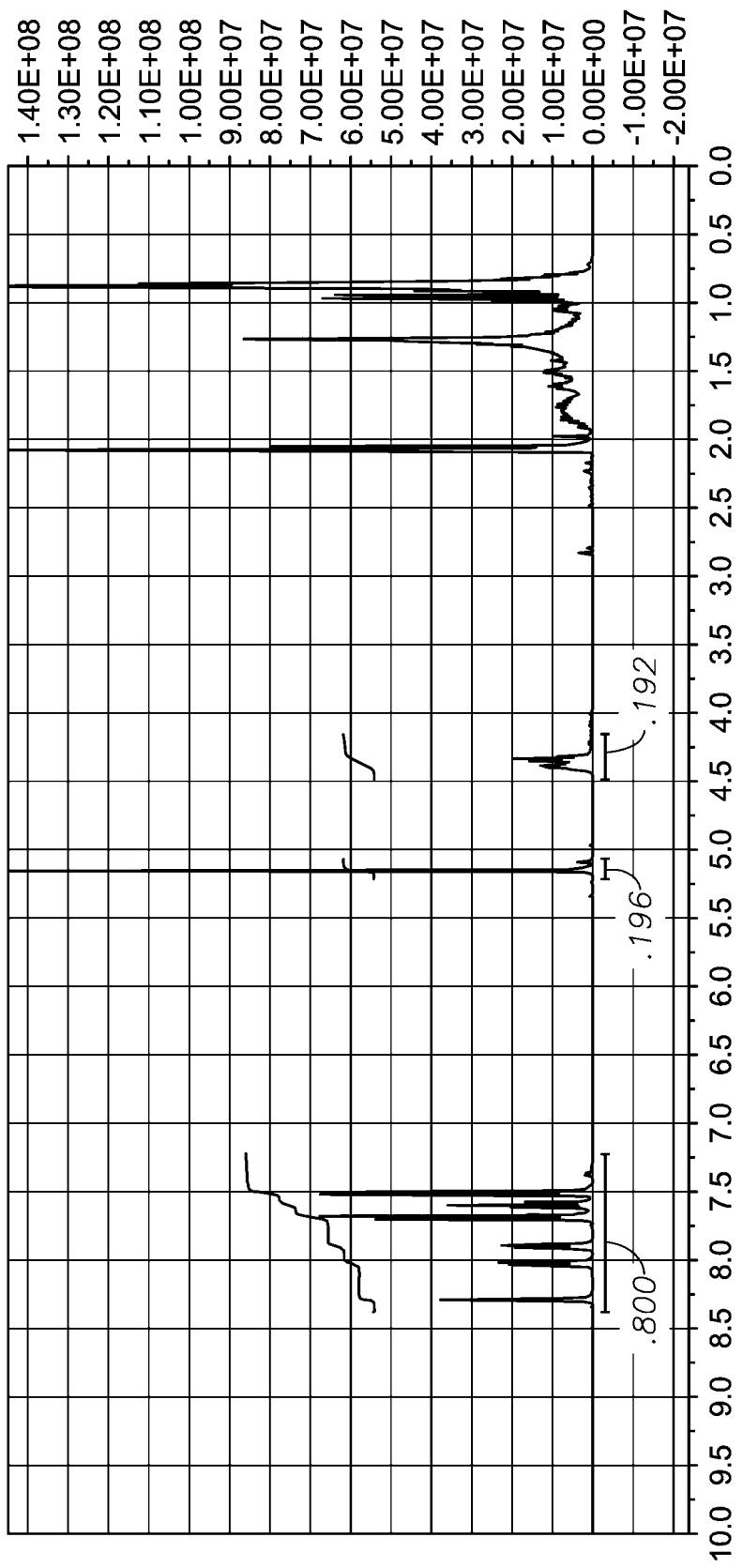
FIG. 3 is the $^1$H NMR spectrum of 4'-acetoxymethylbiphenyl-3-carboxylic acid, isononyl ester as produced in step (c) of the method of Example 1.

(VI)

is shown in FIG. 3.

Example 2

TGA Testing of 4'-acetoxymethylbiphenyl-3-carboxylic acid, isononyl ester

Figure 4:
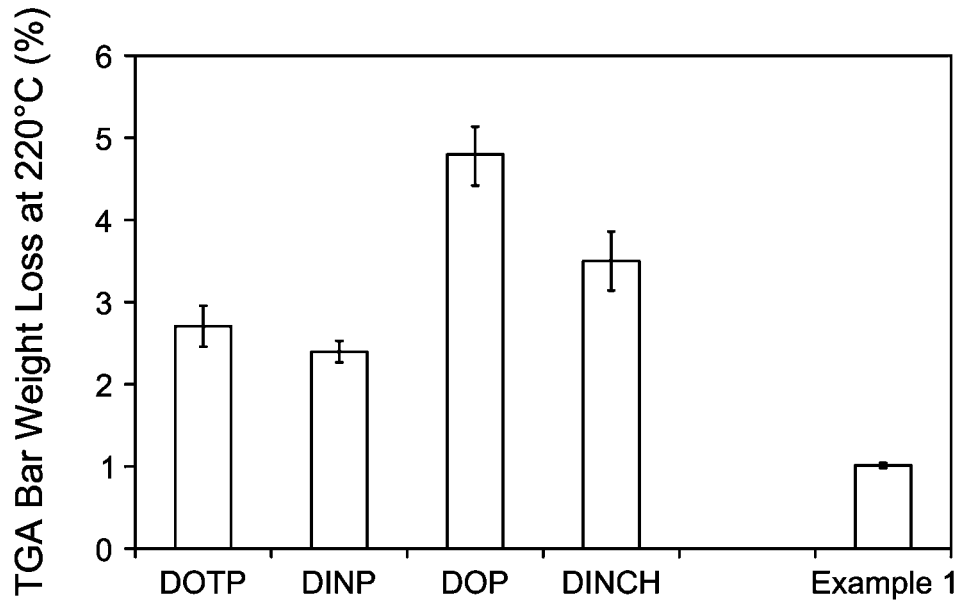
FIG. 4 is a bar graph comparing the TGA volatility of the 4'-acetoxymethylbiphenyl-3-carboxylic acid, isononyl ester produced in Example 1 with that of other known plasticizers.

The 4'-acetoxymethylbiphenyl-3-carboxylic acid, isononyl ester of Example 1 was blended with PVC and subjected to TGA volatility testing using a TA Instruments TGA5000 instrument calibrated to vendor specifications. Sample sizes of 10±1 mg were used. Samples were heated at 10° C./min to 300° C. in nitrogen (25 cc $N_2$/min flow through furnace and 10 cc $N_2$/min flow through balance) and weight loss at 220° C. was used as the volatility metric. The results are shown in FIG. 4, which also shows the results obtained when the same test was conducted with certain known plasticizers, namely dioctyl terephthalate (DOTP), dioctyl phthalate (DOP), diisononyl phthalate (DINP) and 1,2-cyclohexane dicarboxylic acid diisononyl ester (DINCH). It will be seen that the diester of Example 1 had excellent TGA volatility as compared to the other plasticizers tested.

Example 3

Flex Testing of 4'-acetoxymethylbiphenyl-3-carboxylic acid, isononyl ester

The 4'-acetoxymethylbiphenyl-3-carboxylic acid, isononyl ester of Example 1 was blended with PVC and was subjected to low temperature flexibility testing using a TA Instruments Q800 Dynamic Mechanical Analyzer (DMA) with a three-point bending clamp. Samples were cooled at 3° C./min and data was collected upon heating at 3° C./min using a frequency of 1 Hz, amplitude of 20 μm, 0.01 N preload force, and 120% force track. From the DMA measurements, flex onset was determined from the onset of the tan δ peak.

Figure 5:
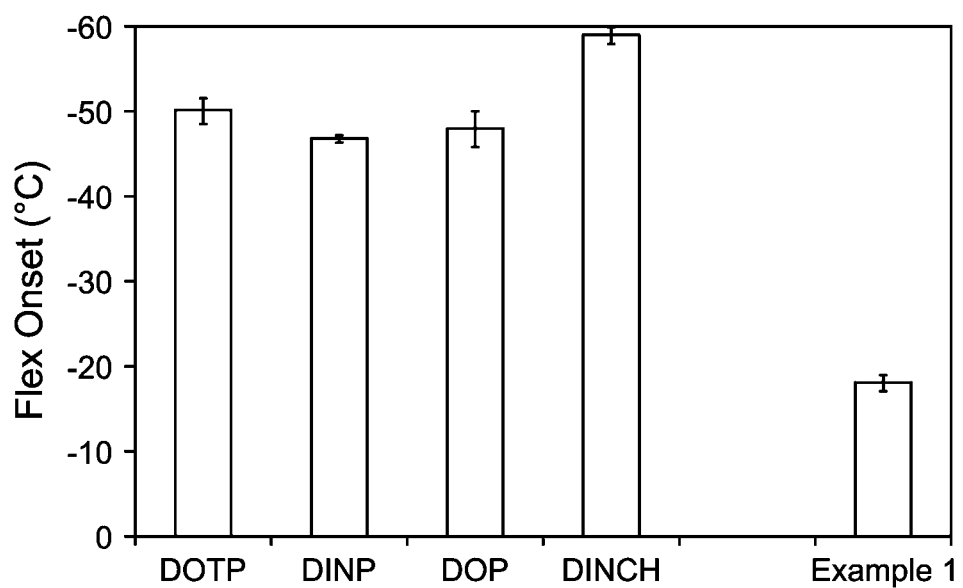
FIG. 5 is a bar graph comparing the flex onset temperature of the 4'-acetoxymethylbiphenyl-3-carboxylic acid, isononyl ester produced in Example 1 with that of other known plasticizers.

The results are shown in FIG. 5, which also shows the results obtained when the same test was conducted with the known plasticizers DOTP, DOP, DINP and DINCH. It will be seen that the diester of Example 1 had adequate low temperature flexibility, although was somewhat worse than the other plasticizers tested.

Example 4

Figure 6:
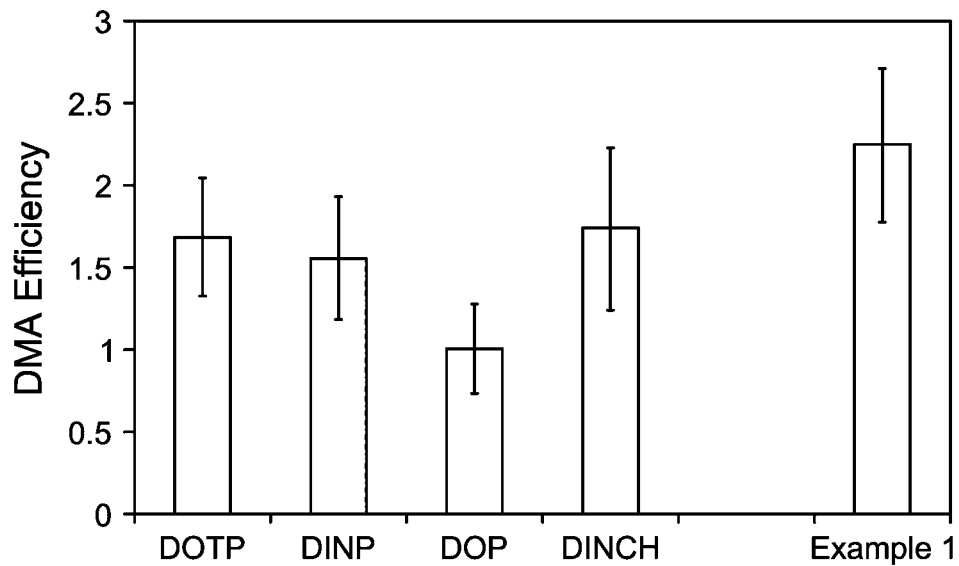
FIG. 6 is a bar graph comparing the results of dynamic mechanical analysis (DMA) of the 4'-acetoxymethylbiphenyl-3-carboxylic acid, isononyl ester produced in Example 1 with those of other known plasticizers.

DMA Efficiency Testing of 4'-acetoxymethylbiphenyl-3-carboxylic acid, isononyl ester The 4'-acetoxymethylbiphenyl-3-carboxylic acid, isononyl ester of Example 1 was subjected to dynamic mechanical analysis (DMA) testing as described in Example 3. DMA efficiency was calculated as the ratio of the storage modulus at 25° C. of the compound sample to that of compound made with DOP. In this evaluation, lower DMA efficiency values indicate less plasticizer is required to achieve the same flexibility at 25° C. The results are shown in FIG. 6, which also shows the results obtained when the same test was conducted with the known plasticizers DOTP, DOP, DINP and DINCH. It is seen that the diester of Example 1 had similar efficiency to the other plasticizers tested.

Example 5

PVC Compatability Testing of 4'-acetoxymethylbiphenyl-3-carboxylic acid, isononyl ester The 4'-acetoxymethylbiphenyl-3-carboxylic acid, isononyl ester of Example 1 was subjected to dynamic mechanical analysis (DMA) testing as described in Example 3. DMA compatibility was evaluated from quantification of the asymmetry of the tan δ peak by calculating the normalized difference in the tan δ equidistant from the peak using:

$$\text{asymmetry} = \frac{1}{\#\Delta x} \sum_{\Delta x} [y(x_{pk} - \Delta x) - y(x_{pk} + \Delta x)]^2$$

where the peak is represented by $y(x_{pk})$, $\Delta x = |x - x_{pk}|$, and $\#\Delta x$ represents the smaller number of data points on either side of the peak. Compatible systems are expected to exhibit a symmetric tan δ peak and yield lower DMA compatibility values.

Figure 7:
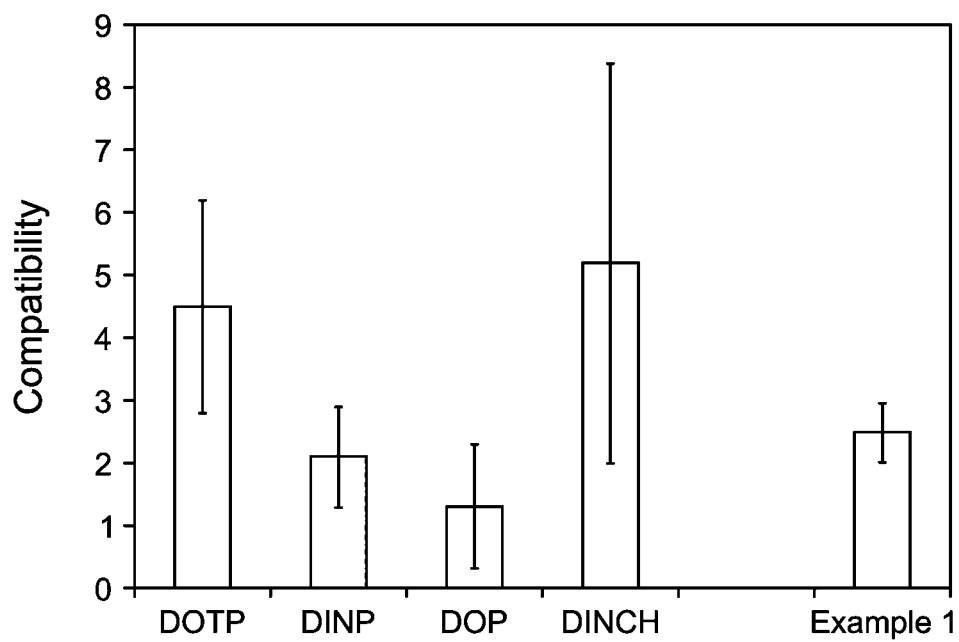
FIG. 7 is a bar graph comparing the compatibility with PVC for the 4'-acetoxymethylbiphenyl-3-carboxylic acid, isononyl ester produced in Example 1 with that of other known plasticizers.

The results are shown in FIG. 7, which also shows the results obtained when the same test was conducted with the known plasticizers DOTP, DOP, DINP and DINCH. It is seen that the diester of Example 1 had similar PVC compatability to the other plasticizers tested.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group consisting of," or "is" preceding the recitation of the composition, element, or elements and vice versa.

What is claimed is:

1. A biphenyl diester having the formula (I):

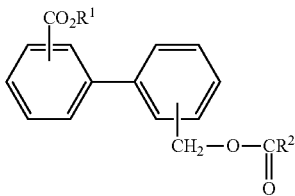

(I)

wherein $R^1$ is an alkyl group having 5 to 15 carbon atoms and $R^2$ is a methyl group or a phenyl group.

2. The biphenyl diester of claim 1, wherein $R^1$ is an alkyl group having 7 to 14 carbon atoms.

3. The biphenyl diester of claim 1, wherein $R^1$ is an alkyl group having 9 to 13 carbon atoms.

4. The biphenyl diester of claim 1, wherein $R^2$ is a methyl group.

5. An isomeric mixture of the biphenyl diesters of claim 1, comprising less than 10 wt % of the 2,X' isomers, where X' is 2', 3' or 4'.

6. A process for producing the biphenyl diester of claim 1, the process comprising:
  (a) contacting a dimethyl biphenyl compound having the formula (II):

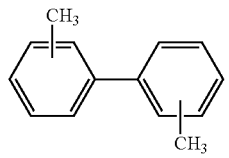

(II)

with oxygen in the presence of a solvent comprising acetic acid and/or benzoic acid under conditions effective to oxidize at least part of the dimethyl biphenyl compound to produce an oxidation product comprising a biphenyl monoester having the formula (III):

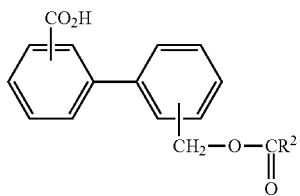

(III)

wherein $R^2$ is a methyl group or a phenyl group; and
  (b) reacting at least part of the biphenyl monoester having the formula (III) with an alcohol having 5 to 15 carbon atoms under conditions effective to produce said biphenyl diester.

7. The process of claim 6, wherein the solvent comprises acetic acid.

8. The process of claim 6, wherein the conditions in the contacting (a) include a temperature from 50 to 200° C.

9. The process of claim 6, wherein the contacting (a) is conducted in the presence of a catalyst comprising cobalt and/or manganese.

10. The process of claim 9, wherein the contacting (a) is conducted at a molar ratio of dimethyl biphenyl compound to catalyst from 1:0.1 to 1:1.

11. The process of claim 6, wherein the oxygen concentration in the gas phase during the contacting (a) is less than 5% by volume.

12. The process of claim 6 and further comprising:
  (c) separating at least part of the biphenyl monoester having the formula (III) from the oxidation product prior to (b).

13. The process of claim 6 and further comprising:
  (1) contacting a feed comprising toluene and hydrogen with a hydroalkylation catalyst under conditions effective to produce a hydroalkylation product comprising (methylcyclohexyl)toluene; and
  (2) dehydrogenating at least part of the hydroalkylation product in the presence of a dehydrogenation catalyst under conditions effective to produce a dehydrogenation product comprising the dimethyl biphenyl compound having the formula (II).

14. The process of claim 13, wherein the hydroalkylation catalyst comprises an acidic component and a hydrogenation component.

15. The process of claim 14, wherein the acidic component of the hydroalkylation catalyst comprises a molecular sieve.

16. The process of claim 15, wherein the molecular sieve is selected from the group consisting of BEA, FAU and MTW structure type molecular sieves, molecular sieves of the MCM-22 family and mixtures thereof.

17. The process of claim 15, wherein the molecular sieve comprises a molecular sieve of the MCM-22 family.

18. The process of claim 14, wherein the hydrogenation component of the hydroalkylation catalyst selected from the group consisting of palladium, ruthenium, nickel, zinc, tin, cobalt and compounds and mixtures thereof.

19. The process of claim 13, wherein the conditions in (d) include a temperature from about 100° C. to about 400° C. and a pressure from about 100 to about 7,000 kPa.

20. The process of claim 16, wherein the hydrogenation component of the hydroalkylation catalyst selected from the group consisting of palladium, ruthenium, nickel, zinc, tin, cobalt and compounds and mixtures thereof.

21. The process of claim 17, wherein the hydrogenation component of the hydroalkylation catalyst selected from the group consisting of palladium, ruthenium, nickel, zinc, tin, cobalt and compounds and mixtures thereof.

22. The mixture of claim 5, wherein $R^2$ is a methyl group and $R^1$ is an alkyl group having 9 to 13 carbon atoms.

* * * * *